United States Patent [19]
Berg

[11] Patent Number: 5,391,264
[45] Date of Patent: Feb. 21, 1995

[54] SEPARATION OF ALPHA-PHELLANDRENE FROM D-LIMONENE BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 209,248

[22] Filed: Mar. 14, 1994

[51] Int. Cl.⁶ .................... B01D 3/36; C07C 7/06
[52] U.S. Cl. ........................... 203/57; 203/58; 203/60; 203/62; 203/63; 585/350; 585/860; 585/862; 585/865; 585/866
[58] Field of Search ............... 203/57, 58, 63, 60, 203/62; 585/350, 355, 862, 860, 865, 866

[56] References Cited

U.S. PATENT DOCUMENTS

| | | | |
|---|---|---|---|
| 2,459,433 | 1/1949 | Johnson et al. | 203/65 |
| 2,818,435 | 12/1957 | Bain et al. | 585/355 |
| 3,987,121 | 10/1976 | Koppel et al. | 203/64 |
| 4,136,126 | 1/1979 | Hirschy et al. | 585/355 |
| 4,508,930 | 4/1985 | Wideman et al. | 585/377 |

Primary Examiner—Wilbur Bascomb, Jr.

[57] ABSTRACT alpha-Phellandrene is difficult to separate from d-limonene by conventional distillation or rectification because of the proximity of their boiling points. alpha-Phellandrene can be readily separated from d-limonene by azeotropic distillation. Effective agents are n-butyl acetate and sulfolane.

1 Claim, No Drawings

SEPARATION OF ALPHA-PHELLANDRENE FROM D-LIMONENE BY AZEOTROPIC DISTILLATION

FIELD OF THE INVENTION

This invention relates to a method for separating alpha-phellandrene from d-limonene using certain organic liquids as agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

There are a number of commercial processes which produce complex mixtures of hydrocarbons and oxygenated organic compounds, e.g. turpentine separation. Two of the commonest close boiling compounds in this mixture are alpha-phellandrene and d-limonene. alpha-Phellandrene boils at 175° C., and d-limonene at 178° C. The relative volatility between these two is 1.2 which makes it very difficult to separate them by conventional rectification. Azeotropic distillation would be an attractive method of effecting the separation of alpha-phellandrene from d-limonene if agents can be found that (1) will create a large apparent relative volatility between alpha-phellandrene and d-limonene and (2) are easy to recover from alpha-phellandrene. Table 1 shows the relative volatility required to obtain 99% purity. With no agent, the relative volatility is 1.2 and 68 actual plates are required. With an agent giving a relative volatility of 1.35, only forty-one plates are required.

OBJECTIVE OF THE INVENTION

The object of this invention is to provide a process or method of azeotropic distillation that will enhance the relative volatility of alpha-phellandrene and d-limonene in their separation in a rectification column. It is a further object of this invention to identify organic compounds which in addition to the above constraints, are stable, can be separated from alpha-phellandrene and recyled to the azeotrope column with little decomposition.

TABLE 1

Theoretical and Actual Plates Required vs. Relative Volatility for alpha-Phellandrene - d-Limonene Separation

| Relative Volatility | Theoretical Plates Required At Total Reflux, 99% Purity | Actual Plates Required 75% Efficiency |
| --- | --- | --- |
| 1.2 | 51 | 68 |
| 1.35 | 31 | 41 |

SUMMARY OF THE INVENTION

The objects of this invention are provided by a process for separating alpha-phellandrene from d-limonene which entails the use of certain organic compounds as the agent in azeotropic distillation.

DETAILED DESCRIPTION OF THE INVENTION

TABLE 2

Effective Azeotropic Distillation agents For Separating alpha-Phellandrene From d-Limonene

| Compounds | Relative Volatility |
| --- | --- |
| None | 1.2 |
| Isopropyl ether | 1.3 |
| Methyl ethyl ketoxime | 1.3 |
| Sulfolane | 1.35 |
| Isobutyl acetate | 1.3 |
| n-Butyl acetate | 1.35 |
| Isobornyl acetate | 1.3 |

I have discovered that certain organic compounds will greatly improve the separation of alpha-phellandrene from d-limonene and permit the separation of alpha-phellandrene from d-limonene by rectification when employed as the agent in azeotropic distillation. Table 2 lists the compounds that I have found to be effective. They are isopropyl ether, methyl ethyl ketoxime, sulfolane, isobutyl acetate, n-butyl acetate and isobornyl acetate.

THE USEFULNESS OF THE INVENTION

The usefulness or utility of the invention can be demonstrated by referring to the data presented in Tables 1 and 2. All of the successful agents show that alpha-phellandrene can be separated from d-limonene by means of azeotropic distillation in a rectification column and that the ease of separation as measured by relative volatility is considerable.

WORKING EXAMPLES

Example 1

Sixty grams of alpha-phellandrene, 40 grams of d-limonene and 50 grams of n-butyl acetate were charged to a vapor-liquid equilibrium still and refluxed for five hours. Analysis indicated a vapor composition of 54.3% alpha-phellandrene, 45.7% d-limonene; a liquid composition of 46.8% alpha-phellandrene, 53.2% d-limonene which is a relative volatility of 1.35.

Example 2

Fifty grams of alpha-phellandrene, 80 grams of d-limonene and 150 grams of sulfolane were placed in the stillpot of a 5.6 theoretical plate glass perforated plate rectification column and refluxed for three hours. The overhead composition was 46.7% alpha-phellandrene, 53.3% d-limonene; the bottoms composition was 13.7% alpha-phellandrene, 86.3% d-limonene. This is a relative volatility of 1.35.

I claim:

1. A method for recovering alpha-phellandrene from a mixture of alpha-phellandrene and d-limonene which comprises distilling a mixture of alpha-phellandrene and d-limonene in the presence of an azeotrope forming agent, recovering alpha-phellandrene and the azeotrope forming agent as overhead product and obtaining the d-limonene as bottoms product, wherein said azeotrope forming agent consists of one material selected from the group consisting of isopropyl ether, methyl ethyl ketoxime, sulfolane, isobutyl acetate, n-butyl acetate and isobornyl acetate.

* * * * *